United States Patent
Chartrand

(10) Patent No.: US 9,713,704 B2
(45) Date of Patent: Jul. 25, 2017

(54) PORT RESERVOIR CLEANING SYSTEM AND METHOD

(71) Applicant: Bradley D. Chartrand, Saratoga Springs, NY (US)

(72) Inventor: Bradley D. Chartrand, Saratoga Springs, NY (US)

(*) Notice: Subject to any disclaimer, the term of this patent is extended or adjusted under 35 U.S.C. 154(b) by 744 days.

(21) Appl. No.: 13/852,257

(22) Filed: Mar. 28, 2013

(65) Prior Publication Data

US 2014/0296822 A1    Oct. 2, 2014

(51) Int. Cl.
| | | |
|---|---|---|
| *B08B 9/027* | (2006.01) | |
| *A61M 39/02* | (2006.01) | |
| *A61B 17/34* | (2006.01) | |
| *A61B 90/70* | (2016.01) | |

(52) U.S. Cl.
CPC ..... *A61M 39/0208* (2013.01); *A61B 17/3417* (2013.01); *A61B 90/70* (2016.02); *A61B 2017/3437* (2013.01); *A61B 2017/3441* (2013.01)

(58) Field of Classification Search
None
See application file for complete search history.

(56) References Cited

U.S. PATENT DOCUMENTS

| | | |
|---|---|---|
| 3,094,124 A | 6/1963 | Birtwell |
| 3,438,375 A | 4/1969 | Ericson |
| 3,971,376 A | 7/1976 | Wichterle |
| 3,978,157 A | 8/1976 | Bottenbruch et al. |
| 4,054,139 A | 10/1977 | Crossley |
| 4,142,525 A | 3/1979 | Binard et al. |
| 4,245,635 A | 1/1981 | Kontos |
| 4,248,224 A | 2/1981 | Jones |
| 4,309,994 A | 1/1982 | Grunwald |
| 4,403,983 A | 9/1983 | Edelman et al. |
| 4,405,305 A | 9/1983 | Stephen et al. |

(Continued)

FOREIGN PATENT DOCUMENTS

| | | |
|---|---|---|
| AU | 2009320117 B1 * | 6/2010 |
| WO | WO 9818506 A1 * | 5/1998 |

OTHER PUBLICATIONS

International Search Report for PCT-US-08-010520 ISR, dated Feb. 24, 2009.

(Continued)

*Primary Examiner* — Eric Golightly
(74) *Attorney, Agent, or Firm* — Zachary F. Madonna

(57) ABSTRACT

A method for cleaning a port reservoir, the method comprising: providing a port reservoir cleaning system, the system comprising: a trocar comprising a proximal end and distal end, the distal end terminating in a sharp tip, a cannula comprising a proximal end, a distal end and a cannula lumen extending therebetween, and a cleaning member comprising a proximal end, a distal end, a shaft and a cleaning member lumen extending therebetween, wherein a portion of the distal end of the shaft is flexible; advancing the trocar and cannula as an assembly through a septum fluidly sealing the port reservoir; withdrawing the trocar from the cannula lumen; advancing the distal end of the cleaning member through the cannula lumen and into the reservoir; rotating the cleaning member; and supplying negative pressure to a lumen of the cleaning member.

8 Claims, 7 Drawing Sheets

(56) References Cited

U.S. PATENT DOCUMENTS

| | | | |
|---|---|---|---|
| 4,423,740 A | 1/1984 | Castle et al. |
| 4,425,119 A | 1/1984 | Berglund |
| 4,468,224 A | 8/1984 | Enzmann et al. |
| 4,469,483 A | 9/1984 | Becker et al. |
| 4,483,688 A | 11/1984 | Akiyama |
| 4,543,088 A | 9/1985 | Bootman et al. |
| 4,563,180 A | 1/1986 | Jervis et al. |
| 4,569,673 A | 2/1986 | Tesi |
| 4,571,749 A | 2/1986 | Fischell |
| 4,587,954 A | 5/1986 | Haber |
| 4,592,920 A | 6/1986 | Murtfeldt |
| 4,603,152 A | 7/1986 | Laurin et al. |
| 4,623,327 A | 11/1986 | Mahurkar |
| 4,645,495 A | 2/1987 | Vaillancourt |
| 4,673,394 A | 6/1987 | Fenton, Jr. et al. |
| 4,692,146 A | 9/1987 | Hilger |
| 4,710,174 A | 12/1987 | Moden et al. |
| 4,767,410 A | 8/1988 | Moden et al. |
| 4,769,005 A | 9/1988 | Ginsburg et al. |
| 4,778,452 A | 10/1988 | Moden et al. |
| 4,781,680 A | 11/1988 | Redmond et al. |
| 4,781,695 A | 11/1988 | Dalton |
| 4,804,359 A | 2/1989 | Grunwald et al. |
| 4,808,156 A | 2/1989 | Dean |
| 4,822,341 A | 4/1989 | Colone |
| 4,838,873 A | 6/1989 | Landskron et al. |
| 4,857,053 A | 8/1989 | Dalton |
| 4,886,501 A | 12/1989 | Johnston et al. |
| 4,886,502 A | 12/1989 | Poirier et al. |
| 4,892,518 A | 1/1990 | Cupp et al. |
| 4,897,081 A | 1/1990 | Poirier et al. |
| 4,902,503 A | 2/1990 | Umemura et al. |
| 4,929,236 A | 5/1990 | Sampson |
| 4,944,726 A | 7/1990 | Hilal et al. |
| 4,954,130 A | 9/1990 | Edwards |
| 4,955,861 A | 9/1990 | Enegren et al. |
| 4,966,586 A | 10/1990 | Vaillancourt |
| 4,983,162 A | 1/1991 | Metais et al. |
| 5,013,304 A | 5/1991 | Russell et al. |
| 5,019,096 A | 5/1991 | Fox, Jr. et al. |
| 5,041,098 A | 8/1991 | Loiterman et al. |
| 5,053,013 A | 10/1991 | Ensminger et al. |
| 5,059,170 A | 10/1991 | Cameron |
| 5,069,206 A | 12/1991 | Crosbie |
| 5,084,015 A | 1/1992 | Moriuchi |
| 5,092,849 A | 3/1992 | Sampson |
| 5,125,893 A | 6/1992 | Dryden |
| 5,129,891 A | 7/1992 | Young |
| 5,133,742 A | 7/1992 | Pinchuk |
| 5,137,529 A | 8/1992 | Watson et al. |
| 5,151,231 A | 9/1992 | Lambert et al. |
| 5,167,638 A | 12/1992 | Felix et al. |
| 5,171,305 A | 12/1992 | Schickling et al. |
| 5,178,612 A | 1/1993 | Fenton, Jr. |
| 5,180,365 A | 1/1993 | Ensminger et al. |
| 5,203,771 A | 4/1993 | Melker et al. |
| 5,205,834 A | 4/1993 | Moorehead et al. |
| 5,213,574 A | 5/1993 | Tucker |
| D337,637 S | 7/1993 | Tucker |
| 5,229,431 A | 7/1993 | Pinchuk |
| 5,236,417 A | 8/1993 | Wallis |
| 5,242,415 A | 9/1993 | Kantrowitz et al. |
| 5,249,598 A | 10/1993 | Schmidt |
| 5,250,038 A | 10/1993 | Melker et al. |
| 5,263,930 A | 11/1993 | Ensminger |
| 5,281,199 A | 1/1994 | Ensminger et al. |
| 5,281,205 A | 1/1994 | McPherson |
| 5,300,048 A | 4/1994 | Drewes, Jr. et al. |
| 5,312,332 A * | 5/1994 | Bales | A61B 17/00234 604/28 |
| 5,312,337 A | 5/1994 | Flaherty et al. |
| 5,318,545 A | 6/1994 | Tucker |
| 5,330,449 A | 7/1994 | Prichard et al. |
| 5,350,360 A | 9/1994 | Ensminger et al. |
| 5,352,204 A | 10/1994 | Ensminger |
| 5,356,381 A | 10/1994 | Ensminger et al. |
| 5,370,624 A | 12/1994 | Edwards et al. |
| 5,372,582 A | 12/1994 | Skrabal et al. |
| 5,373,855 A | 12/1994 | Skrabal et al. |
| 5,387,192 A | 2/1995 | Glantz et al. |
| 5,399,168 A | 3/1995 | Wadsworth, Jr. et al. |
| 5,403,291 A | 4/1995 | Abrahamson |
| 5,405,340 A | 4/1995 | Fageol et al. |
| 5,417,656 A | 5/1995 | Ensminger et al. |
| 5,421,814 A | 6/1995 | Geary |
| 5,423,334 A | 6/1995 | Jordan |
| 5,450,843 A * | 9/1995 | Moll | A61B 17/0218 600/207 |
| 5,458,582 A | 10/1995 | Nakao |
| 5,476,451 A | 12/1995 | Ensminger et al. |
| 5,509,897 A | 4/1996 | Twardowski et al. |
| 5,520,632 A | 5/1996 | Leveen et al. |
| 5,520,643 A | 5/1996 | Ensminger et al. |
| 5,527,277 A | 6/1996 | Ensminger et al. |
| 5,527,278 A | 6/1996 | Ensminger et al. |
| 5,527,307 A | 6/1996 | Srisathapat et al. |
| 5,531,684 A | 7/1996 | Ensminger et al. |
| 5,542,923 A | 8/1996 | Ensminger et al. |
| 5,542,937 A | 8/1996 | Chee et al. |
| 5,549,576 A | 8/1996 | Patterson et al. |
| 5,554,117 A | 9/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,569,182 A | 10/1996 | Twardowski et al. |
| 5,575,769 A | 11/1996 | Vaillancourt |
| 5,607,393 A | 3/1997 | Ensminger et al. |
| 5,613,945 A | 3/1997 | Cai et al. |
| 5,613,974 A | 3/1997 | Andreas et al. |
| 5,614,136 A | 3/1997 | Pepin et al. |
| 5,647,859 A | 7/1997 | Lampropoulos et al. |
| RE35,601 E | 9/1997 | Eckenhoff |
| 5,662,616 A | 9/1997 | Bousquet |
| 5,662,913 A | 9/1997 | Capelli |
| 5,676,656 A | 10/1997 | Brimhall |
| 5,681,289 A | 10/1997 | Wilcox et al. |
| 5,695,490 A | 12/1997 | Flaherty et al. |
| 5,702,363 A | 12/1997 | Flaherty |
| 5,704,915 A | 1/1998 | Melsky et al. |
| 5,713,844 A | 2/1998 | Peyman |
| 5,723,718 A | 3/1998 | Berens |
| 5,725,510 A | 3/1998 | Hartmann et al. |
| 5,741,228 A | 4/1998 | Lambrecht et al. |
| 5,776,096 A | 7/1998 | Fields |
| 5,792,104 A | 8/1998 | Speckman et al. |
| 5,792,123 A | 8/1998 | Ensminger |
| 5,797,886 A | 8/1998 | Roth et al. |
| 5,800,414 A | 9/1998 | Cazal |
| 5,810,776 A | 9/1998 | Bacich et al. |
| 5,810,789 A | 9/1998 | Powers et al. |
| 5,830,172 A | 11/1998 | Leveen et al. |
| 5,830,196 A | 11/1998 | Hicks |
| 5,833,654 A | 11/1998 | Powers et al. |
| 5,836,935 A | 11/1998 | Ashton et al. |
| 5,840,063 A | 11/1998 | Flaherty |
| 5,876,366 A | 3/1999 | Dykstra et al. |
| 5,879,322 A | 3/1999 | Lattin et al. |
| 5,879,333 A | 3/1999 | Smith |
| 5,879,499 A | 3/1999 | Corvi |
| 5,882,341 A | 3/1999 | Bousquet |
| 5,906,596 A | 5/1999 | Tallarida |
| 5,928,174 A | 7/1999 | Gibbins |
| 5,944,688 A | 8/1999 | Lois |
| 5,951,512 A | 9/1999 | Dalton |
| 5,954,691 A | 9/1999 | Prosl |
| 5,957,890 A | 9/1999 | Mann et al. |
| 5,967,490 A | 10/1999 | Pike |
| 5,984,938 A * | 11/1999 | Yoon | A61F 6/206 606/139 |
| 5,989,216 A | 11/1999 | Johnson et al. |
| 6,001,079 A | 12/1999 | Pourchez |
| 6,001,080 A | 12/1999 | Kuracina et al. |
| 6,033,393 A | 3/2000 | Balbierz et al. |

(56) References Cited

U.S. PATENT DOCUMENTS

| | | | |
|---|---|---|---|
| 6,086,555 A | 7/2000 | Eliasen et al. |
| 6,093,180 A | 7/2000 | Elsberry |
| 6,099,508 A | 8/2000 | Bousquet |
| 6,102,884 A | 8/2000 | Squitieri |
| 6,120,492 A | 9/2000 | Finch et al. |
| 6,132,416 A | 10/2000 | Broselow |
| 6,177,522 B1 | 1/2001 | Brady et al. |
| 6,197,845 B1 | 3/2001 | Janssen et al. |
| 6,197,846 B1 | 3/2001 | Combe et al. |
| 6,200,338 B1 | 3/2001 | Solomon et al. |
| 6,213,973 B1 | 4/2001 | Eliasen et al. |
| 6,217,566 B1 | 4/2001 | Ju et al. |
| 6,227,200 B1 | 5/2001 | Crump et al. |
| 6,228,088 B1 | 5/2001 | Miller et al. |
| 6,245,039 B1 | 6/2001 | Brugger et al. |
| 6,280,423 B1 | 8/2001 | Davey et al. |
| 6,355,020 B1 | 3/2002 | Bousquet |
| 6,355,858 B1 | 3/2002 | Gibbins |
| 6,368,658 B1 | 4/2002 | Schwarz et al. |
| 6,375,637 B1 | 4/2002 | Campbell et al. |
| 6,387,105 B1 | 5/2002 | Gifford, III et al. |
| 6,409,700 B1 | 6/2002 | Siegel, Jr. et al. |
| 6,419,643 B1 | 7/2002 | Shimada et al. |
| 6,428,513 B1 | 8/2002 | Abrahamson |
| 6,442,415 B1 | 8/2002 | Bis et al. |
| 6,446,671 B2 | 9/2002 | Armenia et al. |
| 6,447,527 B1 * | 9/2002 | Thompson ......... A61B 17/3494 606/174 |
| 6,517,520 B2 | 2/2003 | Chang et al. |
| 6,530,951 B1 | 3/2003 | Bates et al. |
| 6,545,097 B2 | 4/2003 | Pinchuk et al. |
| 6,575,959 B1 | 6/2003 | Sarge et al. |
| 6,592,544 B1 | 7/2003 | Mooney et al. |
| 6,595,966 B2 | 7/2003 | Davey et al. |
| 6,605,075 B1 | 8/2003 | Burdulis |
| 6,605,751 B1 | 8/2003 | Gibbins et al. |
| 6,610,046 B1 | 8/2003 | Usami et al. |
| 6,629,950 B1 | 10/2003 | Levin |
| 6,630,086 B1 | 10/2003 | Goral et al. |
| 6,638,252 B2 | 10/2003 | Moulton et al. |
| 6,719,727 B2 | 4/2004 | Brimhall et al. |
| 6,777,466 B2 | 8/2004 | Eckstein et al. |
| 6,827,710 B1 | 12/2004 | Mooney et al. |
| 6,897,349 B2 | 5/2005 | Gibbins et al. |
| 6,929,631 B1 | 8/2005 | Brugger et al. |
| 6,938,668 B2 | 9/2005 | Whicher et al. |
| 6,939,357 B2 | 9/2005 | Navarro et al. |
| 6,962,580 B2 | 11/2005 | Adams et al. |
| 6,997,914 B2 | 2/2006 | Smith et al. |
| 7,070,591 B2 | 7/2006 | Adams et al. |
| 7,179,849 B2 | 2/2007 | Terry |
| 7,186,239 B2 | 3/2007 | Woehr |
| 7,261,708 B2 | 8/2007 | Raulerson |
| 7,264,858 B2 | 9/2007 | Belliveau et al. |
| 7,351,233 B2 | 4/2008 | Parks |
| 7,410,602 B2 | 8/2008 | Davey et al. |
| 7,731,700 B1 | 6/2010 | Schytte |
| 7,785,302 B2 | 8/2010 | Powers |
| 7,947,022 B2 | 5/2011 | Amin et al. |
| 7,959,615 B2 | 6/2011 | Stats et al. |
| 8,021,324 B2 | 9/2011 | Bizup et al. |
| 8,025,639 B2 | 9/2011 | Powers et al. |
| 8,029,482 B2 | 10/2011 | Maniar et al. |
| 8,177,762 B2 | 5/2012 | Beasley et al. |
| 8,202,259 B2 | 6/2012 | Evans et al. |
| 8,257,325 B2 | 9/2012 | Schweikert et al. |
| D676,955 S | 2/2013 | Orome |
| 8,382,723 B2 | 2/2013 | Powers et al. |
| 8,382,724 B2 | 2/2013 | Maniar et al. |
| D682,416 S | 5/2013 | Trebella |
| 8,475,417 B2 | 7/2013 | Powers et al. |
| 8,545,460 B2 | 10/2013 | Beasley et al. |
| 8,574,204 B2 | 11/2013 | Bourne et al. |
| 8,585,663 B2 | 11/2013 | Powers et al. |
| 8,591,483 B2 | 11/2013 | Zinn |
| 8,603,052 B2 | 12/2013 | Powers et al. |
| 8,608,713 B2 | 12/2013 | Beasley et al. |
| 8,641,676 B2 | 2/2014 | Butts et al. |
| 8,641,688 B2 | 2/2014 | Powers et al. |
| 8,657,795 B2 | 2/2014 | Magalich et al. |
| 8,715,244 B2 | 5/2014 | Prechtel et al. |
| 8,753,357 B2 | 6/2014 | Roorda et al. |
| 8,805,478 B2 | 8/2014 | Powers et al. |
| 8,852,160 B2 | 10/2014 | Schweikert et al. |
| 8,932,271 B2 | 1/2015 | Hamatake et al. |
| 8,939,947 B2 | 1/2015 | Maniar et al. |
| 8,998,860 B2 | 4/2015 | Sheetz et al. |
| 9,033,931 B2 | 5/2015 | Young et al. |
| 9,039,717 B2 | 5/2015 | Blatter et al. |
| 9,050,407 B2 | 6/2015 | Shih et al. |
| 9,072,880 B2 | 7/2015 | Phillips et al. |
| 9,079,004 B2 | 7/2015 | Wiley et al. |
| 9,149,620 B2 | 10/2015 | Fisher et al. |
| 9,168,365 B2 | 10/2015 | Bourne et al. |
| 9,179,901 B2 | 11/2015 | Young et al. |
| 9,248,268 B2 | 2/2016 | Wiley et al. |
| 9,265,912 B2 | 2/2016 | Draper et al. |
| 2001/0016717 A1 | 8/2001 | Haarala et al. |
| 2001/0056266 A1 | 12/2001 | Tallarida et al. |
| 2002/0082559 A1 | 6/2002 | Chang et al. |
| 2002/0091362 A1 | 7/2002 | Maginot et al. |
| 2002/0138068 A1 | 9/2002 | Watson et al. |
| 2003/0065355 A1 | 4/2003 | Weber |
| 2003/0135168 A1 | 7/2003 | Benchetrit |
| 2003/0203991 A1 | 10/2003 | Schottman et al. |
| 2003/0220628 A1 | 11/2003 | Klisch et al. |
| 2004/0064086 A1 | 4/2004 | Gottlieb et al. |
| 2004/0068241 A1 | 4/2004 | Fischer |
| 2004/0068251 A1 | 4/2004 | Chan et al. |
| 2004/0068315 A1 | 4/2004 | Chandrasekaran et al. |
| 2004/0073171 A1 | 4/2004 | Rogers et al. |
| 2004/0076582 A1 | 4/2004 | Dimatteo et al. |
| 2004/0131863 A1 | 7/2004 | Belliveau et al. |
| 2004/0133173 A1 | 7/2004 | Edoga et al. |
| 2004/0167463 A1 | 8/2004 | Zawacki et al. |
| 2004/0171747 A1 | 9/2004 | Zhong |
| 2004/0199128 A1 | 10/2004 | Morris et al. |
| 2004/0204691 A1 | 10/2004 | Yashiro et al. |
| 2004/0243103 A1 | 12/2004 | King et al. |
| 2005/0010275 A1 | 1/2005 | Sahatjian et al. |
| 2005/0013988 A1 | 1/2005 | Fu et al. |
| 2005/0033237 A1 | 2/2005 | Fentress et al. |
| 2005/0059958 A1 | 3/2005 | Lessard et al. |
| 2005/0104255 A1 | 5/2005 | Mejlhede et al. |
| 2005/0119724 A1 | 6/2005 | Phaneuf et al. |
| 2005/0124980 A1 | 6/2005 | Sanders |
| 2005/0131356 A1 | 6/2005 | Ash et al. |
| 2005/0137580 A1 | 6/2005 | Raulerson et al. |
| 2005/0182352 A1 | 8/2005 | DiMatteo et al. |
| 2005/0192546 A1 | 9/2005 | Griego et al. |
| 2005/0216074 A1 | 9/2005 | Sahatjian et al. |
| 2005/0256461 A1 | 11/2005 | DiFiore et al. |
| 2005/0261636 A1 | 11/2005 | Rome et al. |
| 2006/0004325 A1 | 1/2006 | Hamatake et al. |
| 2006/0015086 A1 | 1/2006 | Rasmussen et al. |
| 2006/0052757 A1 | 3/2006 | Fischer et al. |
| 2006/0064159 A1 | 3/2006 | Porter et al. |
| 2006/0100592 A1 | 5/2006 | Eliasen |
| 2006/0178648 A1 | 8/2006 | Barron et al. |
| 2006/0189922 A1 | 8/2006 | Amarasinghe et al. |
| 2006/0247584 A1 | 11/2006 | Sheetz et al. |
| 2006/0264833 A1 | 11/2006 | Moulton |
| 2007/0078385 A1 | 4/2007 | Accisano et al. |
| 2007/0161940 A1 | 7/2007 | Blanchard et al. |
| 2007/0167925 A1 | 7/2007 | Jacqmein |
| 2007/0191771 A1 | 8/2007 | Moyer |
| 2007/0219497 A1 | 9/2007 | Johnson et al. |
| 2007/0255237 A1 | 11/2007 | Lobl et al. |
| 2007/0260221 A1 | 11/2007 | Chesnin |
| 2007/0270754 A1 | 11/2007 | Soderholm et al. |
| 2007/0287967 A1 | 12/2007 | Hekmat et al. |
| 2008/0108975 A1 | 5/2008 | Appling et al. |
| 2008/0234659 A1 | 9/2008 | Cheng et al. |
| 2008/0294111 A1 | 11/2008 | Tal et al. |

(56) References Cited

U.S. PATENT DOCUMENTS

| | | | |
|---|---|---|---|
| 2008/0306465 | A1 | 12/2008 | Bailey et al. |
| 2009/0036768 | A1 | 2/2009 | Seehusen et al. |
| 2009/0171319 | A1 | 7/2009 | Guo et al. |
| 2009/0171436 | A1 | 7/2009 | Casanova et al. |
| 2009/0204074 | A1 | 8/2009 | Powers et al. |
| 2009/0216216 | A1 | 8/2009 | Powers et al. |
| 2009/0306606 | A1 | 12/2009 | Lancette et al. |
| 2009/0326515 | A1 | 12/2009 | Kagan |
| 2010/0049147 | A1 | 2/2010 | Tanikawa et al. |
| 2010/0106094 | A1 | 4/2010 | Fisher et al. |
| 2010/0191165 | A1 | 7/2010 | Appling et al. |
| 2011/0071500 | A1 | 3/2011 | Lareau |
| 2011/0098662 | A1 | 4/2011 | Zinn |
| 2011/0160673 | A1 | 6/2011 | Magalich et al. |
| 2011/0184353 | A1 | 7/2011 | DeMaria |
| 2011/0264058 | A1 | 10/2011 | Linden et al. |
| 2012/0095440 | A1 | 4/2012 | Islam |
| 2012/0184925 | A1 | 7/2012 | Grant |
| 2012/0232472 | A1 | 9/2012 | Bhagchandani et al. |
| 2013/0060200 | A1 | 3/2013 | Dalton et al. |
| 2013/0150811 | A1 | 6/2013 | Horgan |
| 2014/0058332 | A1 | 2/2014 | Bourne et al. |
| 2014/0236105 | A1 | 8/2014 | Hanson et al. |
| 2014/0296790 | A1 | 10/2014 | Chartrand et al. |
| 2014/0296882 | A1 | 10/2014 | Roorda et al. |
| 2016/0001055 | A1 | 1/2016 | Bourne et al. |
| 2016/0121094 | A1 | 5/2016 | Nardone et al. |

OTHER PUBLICATIONS

International Search Report for PCT-US-08-010520 WOSA, dated Feb. 24, 2009.
McCarthy, et al, The Use of a Flow Rate Injctor for Contrast-Enhanced CT, Radiology, 1984, 151:800.
Ireland, et al, Safety and Convenience of a Mechanical Injector Pump for Conorary Angiography, Catheterization and Cardiovascular Diagnosis, 1989, 16:199-201.
Miles, et al, Safe use of an Intravenous Power Injector for CT: Experience and Protocol, RSNA, 1990, pp. 69-70.
Darlson, et al, Safety Considerations in the Power Injection of Contrast Media Via Central Venous Catheters During Domputed Tomographic Examinations, Investigative Radiology vol. 27, 1992, pp. 337 - 340.
Steinbach, et al, Breast Implants, Common Complications, and Concurrent Breast Disease, RadioGraphics 1993, 13:95-118.
Vergara, Adverse Reactions to Contrast Media in CT: Effects of Temperature and Ionic Property, Radiology 1996, 199:363-366.
Herts, et al, Power Injection of Contrast Material through Central Venous Catheters for CT: In Vitro Evaluation, Radiology 1996, 200:731-735.
Kaste, et al, Safe Use of Power Injectors with Central and Peripheral Venous Access Devices for Pediatric CT, Pediatr Radial, 1996, 36:499-501.
Urquiola, et al, Using Lead Foil as a Radiopaque Marker for Computerized Tomography Imaging when Implant Treatment Planning, Journal of Prosthetic Dentistry vol. 77 No. 2, 1997, pp. 227-228.
Hills, et al, Experience with 100 Consecutive Central Venous Access Arm Ports Placed by Interventional Radiologists, JVIR 1997, 8:983-989.
Ruess, et al, In-line Pressures Generated in Small-Bore Central Venous Catheters During Power Injection of CT Contrast Media, Radiology 1997, 203:625-629.
Herzig, et al, the Use of Power Injection with Radiographic Contrast Media Into PICC Lines, JVIR, vol. 11 Issue 2 Supp. pp. 1-535 p. 308, 2000.
Blot, et al, Accuracy of Totally Implanted ports, tunnelled, single and multiple-lumen contra! venous catheters for measurement of central venous pressure, Intensive Care Med, 2000, pp. 1837-1842.
Herts, et al, Power Injection of Contrast Media Using CVC: Feasibility, Safety, and Efficacy, AJR: 176, pp. 447-453 2001.
Biffi, et al, a Randomized, Prospective Trial of Central Venous Ports Connected to Standard Open-Ended or Groshong Catheters in Adult Oncology Patients, American Cancer Society, 2001, pp. 1204-1212.
User Manual for the ESPrit 3G Speech Processor and Accessories, Nucleus Cochlear Implant Systems 106 pages, 2001.
Salts, et al, Can PICC be Used for Contrast Injection with a CT Power Injector, JVIR vol. 13, Issue 2, Supp S1-S117 p. S13, 2002.
Funaki, Central Venous Access: A Primer for the Diagnostic Radiologist, AJR: 179, 2002, pp. 309-318.
Teichgraber, et al, Central Venous Access Catheters: Radiological Management of Complications, Cardiovasc Intervent Radio!, 2003, 26:321-333.
Bard Access Systems, Inc. PORT User Manual 31 pages, 2003.
Costa, More Than Skin Deep: An Overview of Iodinated Contrast Media, Java vol. 8 No. 4, 2003, pp. 34-39.
Scher, et al, Alternative Graft Materials for Hemodialysis Access, Seminars in Vascular Surgery, vol. 17 No. 1, 2004, pp. 19-24.
Abstracts of the World Apheresis Association 10th Congress, Jornal of Clinical Apheresis, 2004, 18: 20-58.
Costa, Understanding Contrast Media, Journal of Infusion Nursing, pp. 302-312 2004.
Sanelli, Safety and Feasibility of Using a Central Venous Catheter for Rapid Contrast Injection Rates, AJR 183, 2004, pp. 1829-1834.
Patient Safety Advisory, Extravasation of Radiologic Contrast, PSRS, pp. 1-6 2004.
Biffi, et al, Use of Totally Implantable Central Venous Access Ports for High-Dose Chemotherapy and Peripheral Blood Stem Cell Transplantation: results of monocentre series of 376 patients, Annals of Oncology, 15:296-300 2004.
Abstracts from the American Society for Apheresis 26th Annual Meeting, Journal of Clinical Apheresis 20:1-51 2005.
Swindle, et al, Vascular Access Port Usage in Large Animal Species, Contemporary Topics, 2005 vol. 44 No. 27 pp. 7-17.
Gebauer, Contrast Media Pressure Injectoin Using a Portal Catheter System—Results of an in Vitro Study, ROFO 2005, pp. 1417-1423 (German with English abstract).
Hou, et al, Comparisons of Outcomes and Survivals for Two Central Venous Access Port Systems, Journal of Surg Oncology, 2005, 91:61-66.
Swerdlow, Red Cell Exchange in Sickle Cell Disease, American Society of Hematology, 2006, pp. 48-53.
Supplement to Imaging Economics, CIN Strategies: Anticipate, Manage, Prevent, 2007, S1-S18.
Medtronic Synchromed II & Synchromed EL Priming Bolus Reference Card, 2007. 2 pages.
Abtracts from the American Society for Apheresis 29th Annual Meeting, Journal of Clinical Apheresis 23:1-51 2008.
Smith Hartkopf, Implanted Ports, Computed Tomography, Power Injectors, and Catheter Rupture, Clinical Journal of Onology Nursing, vol. 12, No. 5, pp. 809-812 2008.
Biffi, et al, Best Choice of CEntral Venous Insertion Site for the Prevention of Catheter-Related Complications in Adult Patients who need Cancer Therapy: A randomized Trial, Annals of Oncology 20: 935-940 2009.
Abstracts from the American Society for Apheresis 30th Annual Meeting, Journal of Clinical Apheresis 24: 53-94 2009.
Klassen, The Role of Photopheresis in the Treatment of Graft-Versus-Host Disease, Current Oncology vol. 17 No. 2 pp. 55-58 2010.
Abstracts from the American Society for Apheresis 32nd Annual Meeting, Journal of Clinical Apheresis 26:59-100 2011.
Special Issue Abstracts from the 34th Annual Meeting of the American Society for Apheresis, Journal of Clinical Apheresis 28:87-141 2013.
Guiffant, et al, Impact of the Shape of the Implantable Ports on their Efficiency of flow (Injection and Flushing), Medical Devices: Evidence and Research 2014:7, pp. 319-324.
Special Issue Abstracts from the American Society for Apheresis 36th Annual Meeting, Journal of Clinical Apheresis 30:61-133 2015.

(56) References Cited

OTHER PUBLICATIONS

Chand, et al, Use of Vascular Ports for Long-Term Apheresis in Children, J Vasc Intery Radio! 2015, 26: 1669-1672.
Shrestha, et al, Use of a Dual Lumen Port for Automated Red Cell Exchange in Adults with Sickle Cell Disease, Journal of Clinical Apheresis, 2015.
International Search Report for PCT-US-08-078976 WOSA, dated Apr. 3, 2009.
International Search Report for PCT-US-08-078976 ISR, dated Apr. 3, 2009.
International Search Report for PCT-US-08-078976 IPRP, dated Apr. 7, 2010.
International Search Report for PCT-US-08-010520 IPRP, dated Mar. 9, 2010.
International Search Report for PCT-US-03-033373 ISR, dated Mar. 15, 2004.

* cited by examiner

PORT RESERVOIR CLEANING SYSTEM AND METHOD

CROSS-REFERENCE TO RELATED APPLICATIONS

This application claims priority to U.S. provisional application No. 61/617,219 filed on Mar. 29, 2012, incorporated herein by reference in its entirety.

FIELD OF THE INVENTION

The present invention relates generally to a system and method for clearing thrombus formations from the reservoir of an implantable port.

BACKGROUND OF THE INVENTION

Medical professionals often use implantable ports for accessing the vascular system. Ports are typically implanted in the chest and connected to a catheter having a tip positioned at, a particular point within the body, commonly the junction of the superior vena cave and the right atrium. Ports can have one or more reservoirs in fluid communication with ore or more lumens of the catheter. A needle-penetrable and self-sealing septum covers the reservoir, and the reservoir can be accessed with a needle. The needle can be used for infusing or aspirating fluid to and from the tip of the catheter via the reservoir.

The presence of blood within the reservoir commonly leads to thrombus formation as blood platelets adhere and accumulate to the walls of the reservoir. Thrombus formations can occlude the outlet lumen and lead to increased infection rates. Occlusions can affect medical device performance, impairing the ability to infuse or aspirate fluid through the device. When port performance is compromised, medical professionals are often forced to replace the port with a new one, requiring additional surgeries, and increasing costs and risk to the patient. Further, even when the reservoir is only partially occluded, fluid dynamics within the reservoir are suboptimal. There remains a need to reduce the presence of thrombus formation within a port reservoir while minimizing costs and risks to the patient.

SUMMARY OF THE INVENTION

In one aspect, the invention provides a port reservoir cleaning system including a trocar having a proximal end and distal end, the distal end terminating in a sharp tip, a cannula having a proximal end, a distal end and a cannula lumen extending therebetween, and a cleaning member having a proximal end, a distal end, a shaft and a cleaning member lumen extending therebetween. A portion of the distal end of the shaft is flexible.

In another aspect, the invention provides a method for cleaning a port reservoir, the method including providing a port reservoir cleaning system, the system including a trocar, a cannula and a cleaning member having a shaft, where a portion of the distal end of the shaft is flexible. The trocar and cannula are advanced as an assembly through a septum fluidly sealing the port reservoir while the trocar is loaded within a lumen of the cannula. The trocar is withdrawn from the cannula lumen. The distal end of the cleaning member is advanced through the cannula lumen and into the reservoir. The cleaning member is rotated and negative pressure is supplied to a lumen of the cleaning member.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 5 shows cross-sectional views of a port reservoir accessed by a system according to the embodiments of the invention shown in FIGS. 1-3.

DETAILED DESCRIPTION OF THE INVENTION

Figure 1:
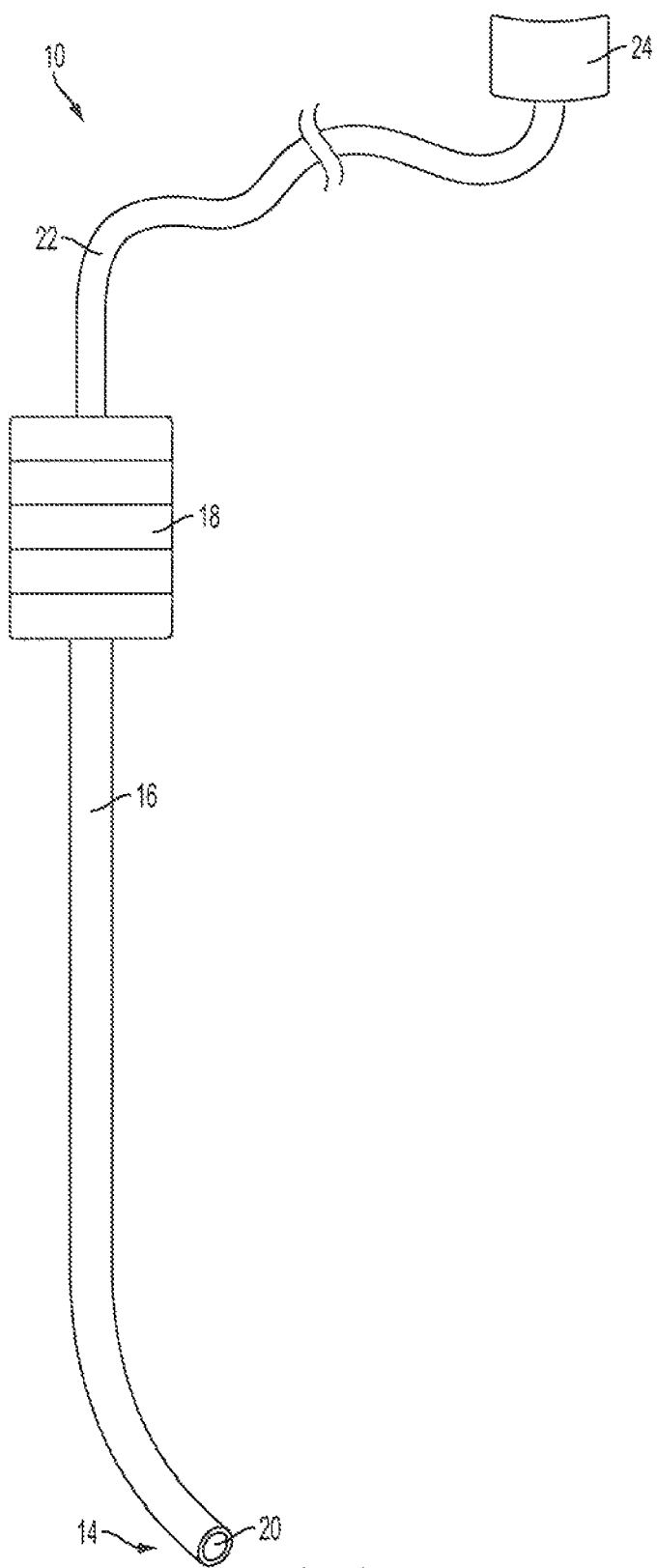
FIG. 1 is a side view of a cleaning member according to an embodiment of the invention.

The present invention can be understood more readily by reference to the following detailed description the examples included therein, and to the Figures and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and not intended to be limiting.

Referring now in detail to the drawings, in which like reference numerals indicate like parts or elements throughout the several views, various embodiments, presented herein is a port reservoir cleaning system and method.

As shown in FIG. 1, a cleaning member 10 according to an embodiment of the invention is formed from a polymer shaft 16 having lumen 20 extending therethrough and terminating in an opening at the distal end 14 of the shaft 16. A hub 18 is connected to the proximal end of the shaft 16. The lumen 20 is in fluid communication with an extension tube 22 and a connection element 24. The hub 18, extension tube 22 and connection element 24 can be made of medical grade plastics and polymers, and manufactured using extrusion and injection molding techniques known in the art.

Figure 2:
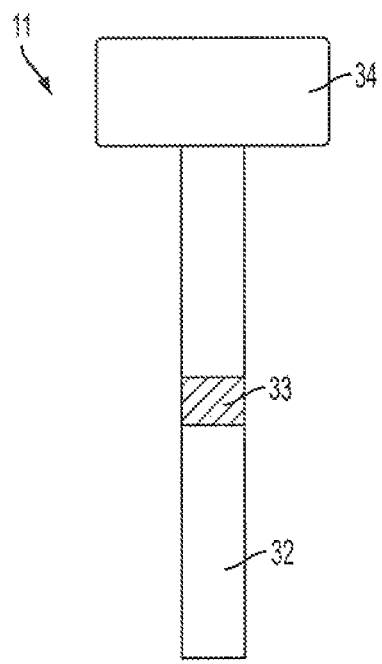
FIG. 2 is a side view of a cannula according to an embodiment of the invention.
Figure 3:
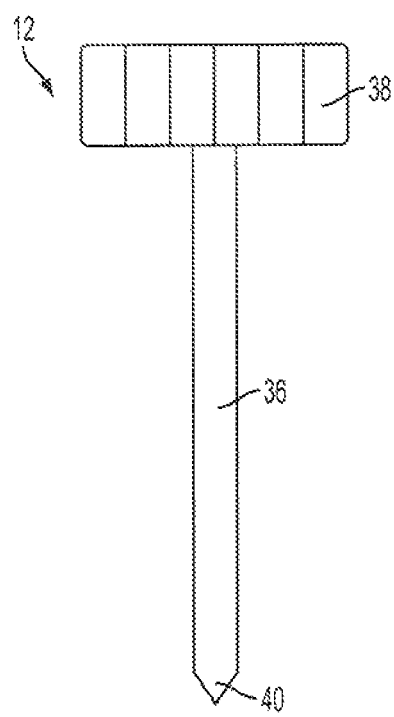
FIG. 3 is a side view of a trocar according to an embodiment of the invention.
Figure 4:
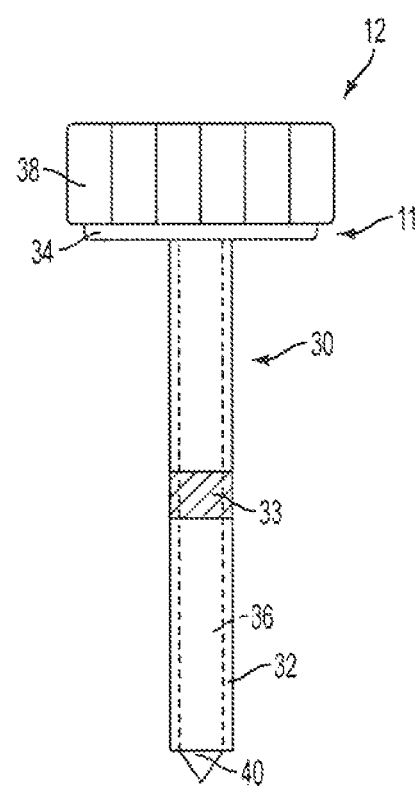
FIG. 4 is a side view of a trocar cannula assembly according to the embodiments of the invention shown in FIGS. 2 and 3.

Cleaning member 10 accesses the port reservoir via a cannula 11 and a trocar 12 as shown in FIGS. 2 and 3. The cannula 1 includes a tube 32 having a valve 33 extending across its lumen. The valve 33 is a self-sealing valve, and can be for example a slit valve or a reed valve. The cannula 11 also includes a hub 34. The trocar 12 has a shaft 36 terminating in a point 40 at its distal end, and a hub 38. The trocar and cannula can be mated as a trocar cannula assembly 30, as shown in FIG. 4. The trocar shaft 36 extends through the cannula 11 lumen such that the tip 40 of the trocar 12 extends just beyond the distal cannula opening. The outside of the hub 34 for the cannula 11 can have engaging member (such as threads) compatible with engaging members on an inside wall of the hub 38 for the trocar 12, so that they can be fixed to one another when formed as an assembly 30. The cannula and trocar shafts can be made of more rigid materials such as plastics or metals, so that they are capable of advancing though the compressed elastomeric septum without kinking or collapsing.

Figure 5A:
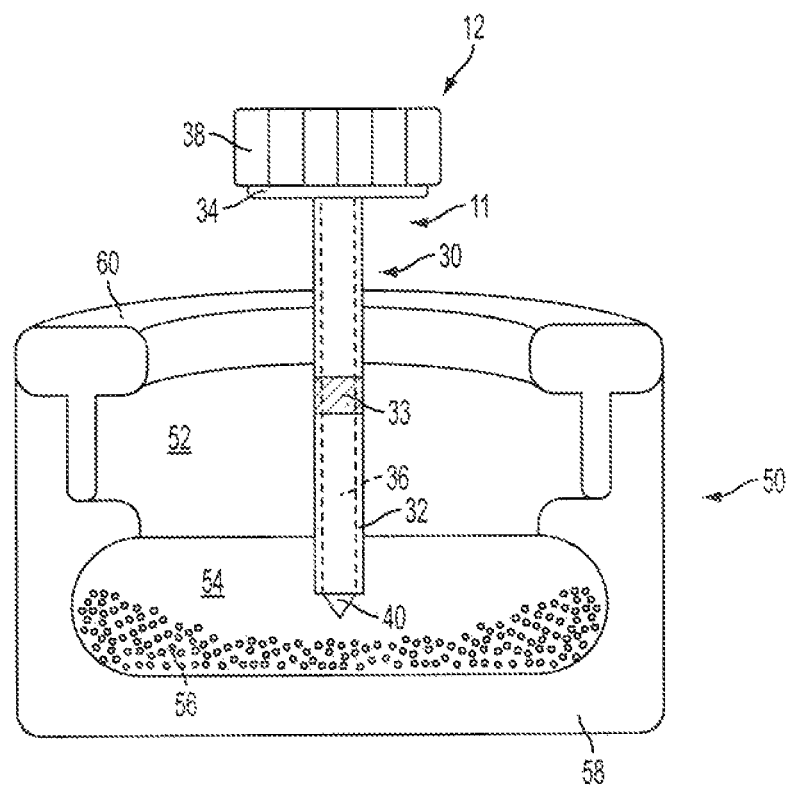
FIG. 5A shows a trocar cannula assembly advanced through a septum and into the port reservoir.
Figure 5B:
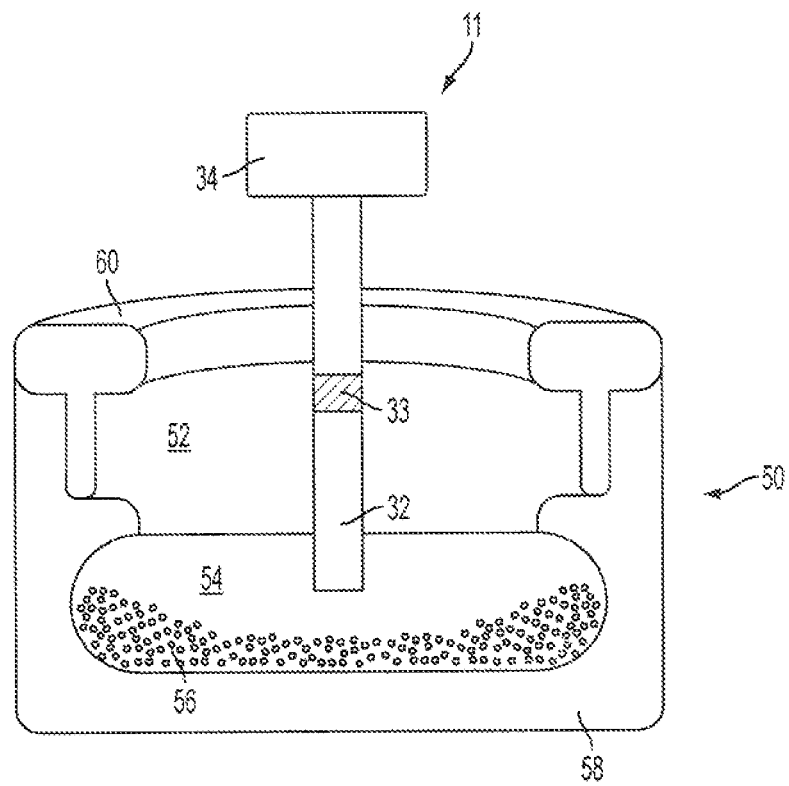
FIG. 5B shows a cannula accessing the reservoir after the trocar has been withdrawn.
Figure 5C:
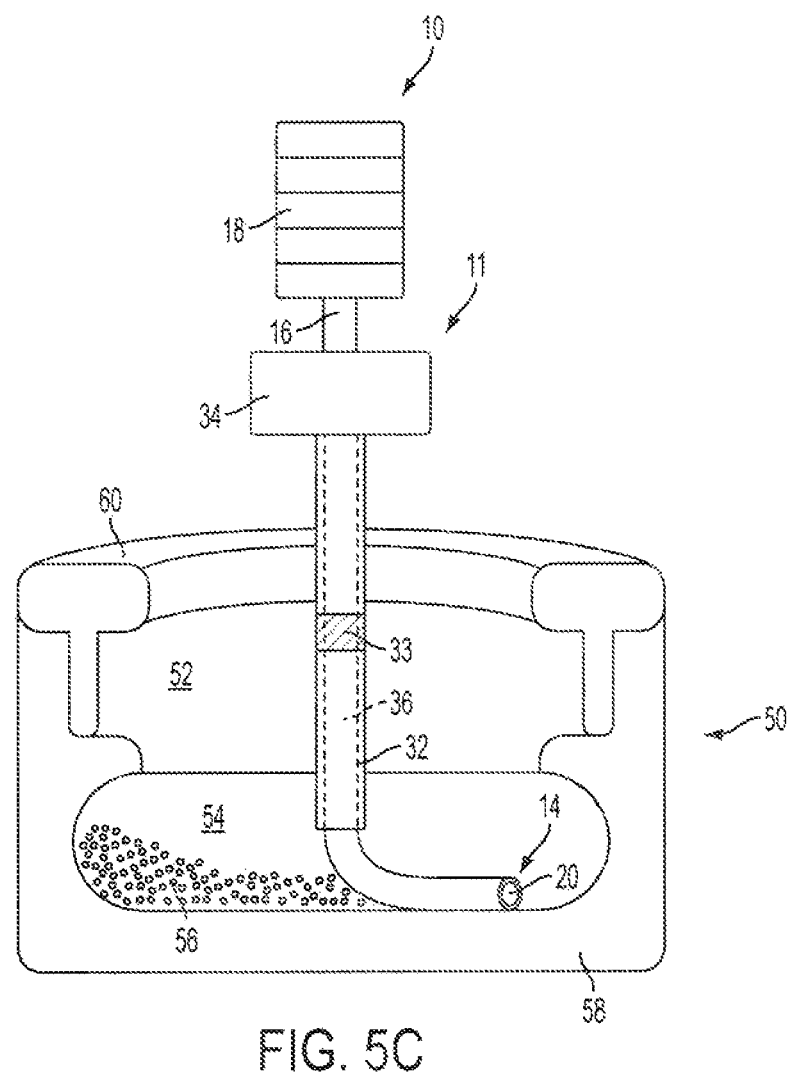
FIG. 5C shows the cleaning device advanced through the cannula and into the reservoir.

FIGS. 5A-5C illustrate how the system of the cleaning member 10, cannula 11 and trocar 12 can be used to access and clean thrombus formations from the port reservoir. As shown in FIG. 5A, a typical port 50 has a port body 58 defining one or more walls of a reservoir 54. The reservoir 54 is fluidly sealed by an elastomeric septum 52, and the septum 52 is held to the port body 58 by a retaining ring 60. To provide for the cleaning device 10 to the reservoir 54, the tracer cannula assembly 30 is advanced through the port septum 52 so that the distal ends of the assembly enter the reservoir. The trocar 12 is subsequently withdrawn from the lumen of the cannula 11, and the cannula 11 remains, providing access to the reservoir 54, as shown in FIG. 5B. Fluid access to the reservoir is sealed by the valve 33 which automatically seals upon withdrawal of the trocar 12. The cleaning member 10 is then advanced through the lumen of the cannula 11, and the distal end 14 of the cleaning device 10 can be advanced towards the side walls of the reservoir 54, as shown in FIG. 5C.

With the distal end 14 of the cleaning device 10 in fluid communication with the reservoir 54, infusion and aspiration be performed for cleaning surfaces of the reservoir 54 walls. For instance, an anti-coagulant solution such as heparinized saline can be infused into the port to chemically breakup and loosen thrombus formations. The tip of the distal end 14 of the cleaning member 10 can be used to mechanically scrape or abrade the thrombus formations 56, while a negative pressure is simultaneously applied to the cleaning device lumen 20 to aspirate loose pieces of thrombus. The scraping action can be performed by moving the cleaning device 10 in an up and down motion through the cannula 11, while rotating the device 10 to reach all surfaces. The hub 18 can include gripping features to make manipulating the device easier. Suction within the lumen 20 can be also be helpful in preventing chunks of thrombus from passing through the port catheter and into the blood stream, minimizing the risk of an embolism.

Figure 6:
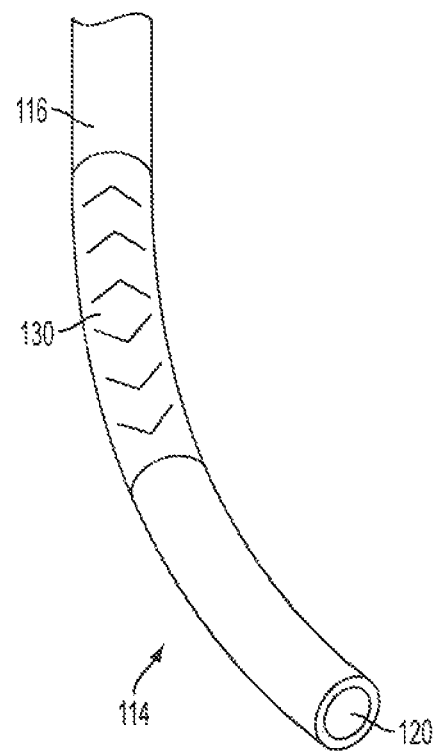
FIG. 6 shows the distal end of a cleaning device having more than one flexural modulus according to an embodiment of the invention.

The cleaning device 10 has a flexible distal end 14 which allows the device to extend outward to edges of the reservoir 54, as shown in FIG. 5C. To aid the mechanical breakup of thrombus 56, aspiration of material, and to reinforce the cannula where it flexes, a portion of the device shaft can be manufactured to have a higher flexural modulus relative to other portions of the shaft, according to an embodiment of the invention as shown in FIG. 6. If the shaft 116 is reinforced with a high flexural modulus around the flex point 130, the distal end 114 of the cleaning device will be biased towards and remain pressed up against reservoir walls. Proximity of the lumen 120 opening to the reservoir wall surfaces facilitates improved aspiration and mechanical breakup of thrombus adhered to reservoir walls. Further, kinking of the shaft 36 at the flex point can be minimized, which will facilitate better aspiration through the lumen 120. The shaft 116 can include a reinforcing technique known in the art, such as thicker shaft side wall, overmolding or co-extrusion of a reinforcing member, a transition to a higher durometer polymer, or other reinforcing techniques known in the art for providing for a higher flexural modulus. To aid insertion of a cleaning member in general, especially in embodiments having a higher flexural modulus at the flex point, the tip of the distal end 114 can taper so that as it is advanced into the reservoir and presses against the bottom surface, it tilts and falls to one side, promoting lateral movement towards a side wall.

Figure 7:
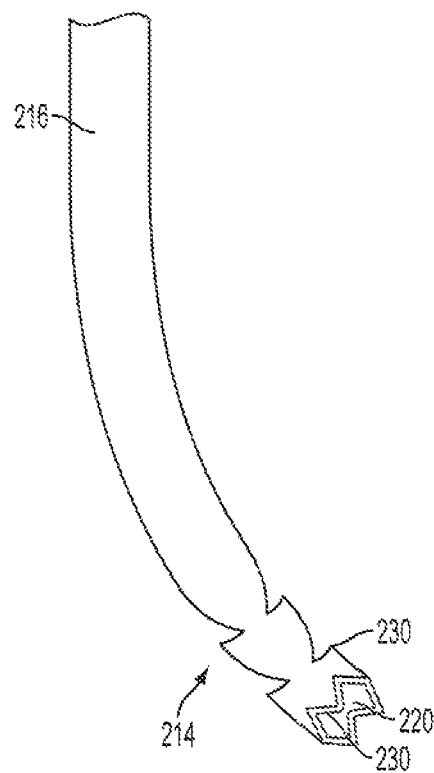
FIG. 7 shows the distal end of a cleaning device having scraping members according to an embodiment of the invention.

The distal end of the cleaning device can also incorporate scraping edges for the mechanical breakup of thrombus buildup according to an embodiment of the invention, as shown in FIG. 7. The shaft 216 can include skived elements 230 cut from the shaft walls and tip of the distal end 214. Scraping edges 230 formed around the distal tip of the lumen 220 can be especially helpful for cleaning the reservoir according to the method of mechanical breakup of thrombus with simultaneously thrombus fragments. The shaft 216 can be coextruded with a high durometer outer layer, so that skived scraping elements have rigid outer edges. Alternatively, scraping elements made of hard materials such as metals can be overmolded or affixed to the distal end 214 of the cleaning device using techniques known in the art. Side holes can be incorporated in the shaft 216 wall for fluid access to the lumen 220, or skived elements can be cut so that openings are cut into shaft 216 side walls as skives are formed. Openings can be located adjacent to scraping members 230 for advantageously aspirating thrombus as it is fragmented by scraping members 230. Hole arrays can also be arranged to uniformly distribute anti-coagulant fluid during infusion functions on inner walls of the reservoir.

Figure 8:
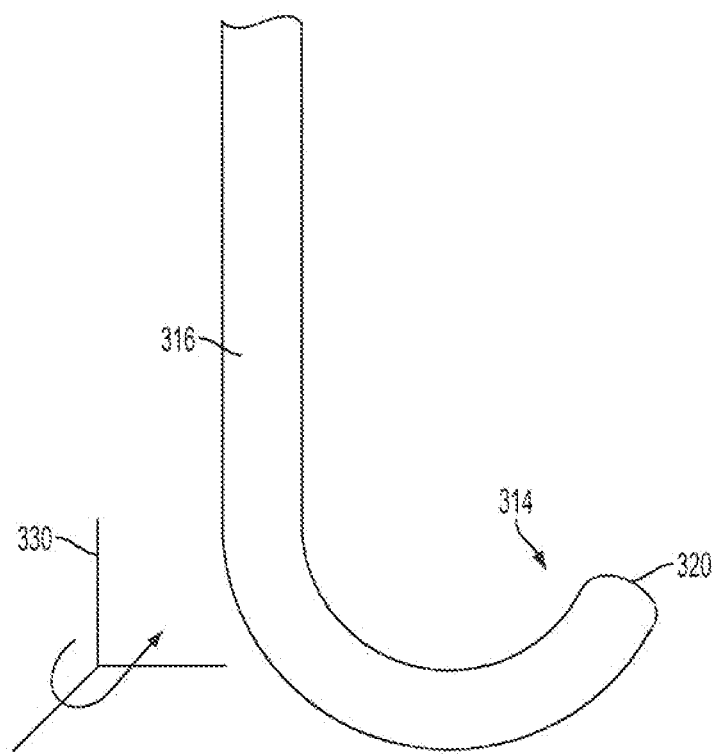
FIG. 8 shows the distal end of a cleaning device having a pre-curved end according to an embodiment of the invention.

Mechanical breakup of thrombus formations can be further facilitated by manufacturing the distal end of the cleaning member shaft in a pre-curved configuration according to an embodiment of the invention, as shown in FIG. 8. The curve can wrap around the longitudinal axis of proximal portions of the shaft 316, as illustrated in the diagram accompanying FIG. 8. With this configuration, the user can twist the device and the tip 320 of the device acts as a leading edge for following along the wall of a contoured reservoir. According to this embodiment, the mechanical breakup of thrombus on surfaces can be improved especially along outer edges of the reservoir. This configuration, like any configuration, can be combined with others to promote contact with the reservoir wall and mechanical breakup of thrombus formations.

Figure 9:
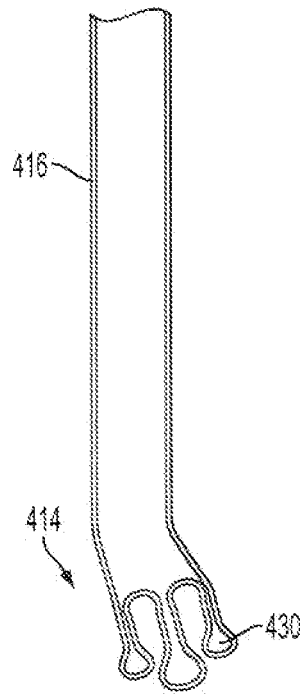
FIG. 9 shows the distal end of a wire element for use with the cleaning member according to an embodiment of the invention.

As shown in FIG. 9, a wire member 416 can be advanced through a system lumen for effectively breaking up or dislodging thrombus. The wire member 416 can have loops 430 or other types of openings at its distal end 414 which can scrape against the reservoir wall and masticate thrombus formations into smaller pieces for aspiration. This wire embodiment can also be fixed to the distal end of the cleaning member. The wire can be a medical grade metal having a shape memory such an nitinol so that the distal end 414 expands after exiting a lumen and being exposed within the reservoir. Alternatively, the wire element can be another hardened or metal element having edges capable of effectively dislodging and/or fragmenting thrombus formations within the reservoir.

What is claimed is:

1. A method for cleaning a port reservoir, the method comprising:
   providing a port reservoir cleaning system, the system comprising:
      a trocar comprising a proximal end and distal end, the distal end terminating in a sharp tip,
      a cannula comprising a proximal end, a distal end and a cannula lumen extending therebetween, and
      a cleaning member comprising a proximal end, a distal end, a shaft and a cleaning member lumen extending therebetween, wherein a portion of the distal end of the shaft is flexible;
   advancing the trocar and cannula as an assembly through a septum fluidly sealing the port reservoir;
   withdrawing the trocar from the cannula lumen;
   advancing the distal end of the cleaning member through the cannula lumen and into the reservoir;
   rotating the cleaning member; and
   supplying negative pressure to a lumen of the cleaning member.

2. The method of claim 1, wherein the cannula further comprises a valve element disposed across the cannula lumen.

3. The method of claim 1, wherein a first portion of the shaft and a second portion of the shaft have a different flexural modulus.

4. The method of claim 1, wherein the distal end of the cleaning member comprises a plurality of scraping members.

5. The method of claim 1, wherein the distal end of the cleaning member is pre-curved and lies in a common plane with the shaft.

6. The method of claim 1, wherein the distal end of the cleaning member is pre-curved and extends away from a plane extending along the length of the shaft.

7. The method of claim 1, wherein the distal end of the cleaning member comprises a wire element.

8. The method of claim 1 further comprising:
   advancing a wire element through the cannula lumen and into the reservoir.

* * * * *